United States Patent [19]

Kordes

[11] Plant 5,157

[45] Dec. 13, 1983

[54] HYBRID GRANDIFLORA ROSE CV. SHREVEPORT

[75] Inventor: Reimer Kordes, Aspern Krs. Pinneberg, Fed. Rep. of Germany

[73] Assignee: Armstrong Nurseries, Inc., Ontario, Calif.

[21] Appl. No.: 388,028

[22] Filed: Jun. 14, 1982

[51] Int. Cl.[3] ..... A01H 5/00

[52] U.S. Cl. ..... Plt./17

[58] Field of Search ..... Plt./17

*Primary Examiner*—James R. Feyrer

*Attorney, Agent, or Firm*—Synnestvedt & Lechner

[57] ABSTRACT

A new hybrid grandiflora rose having the following combination of characteristics: a profusion of brightly colored, well-formed flowers; an abundance of leathery foliage which covers even the lowest branches; it is a vigorous, easy to grow and easy to care for plant having an upright habit and a highly branched bush which lends itself to usefulness for landscaping purposes.

1 Drawing Figure

1

This invention relates to a new class of hybrid Grandiflora rose cv. "Shreveport". The plant is a hardy outdoor seedling of the bush type, cultivated for garden decoration. It was hybridized by Reimer Kordes in Sparrieshoop, Holstein, West Germany, by crossing "Zorina", U.S. Plant Pat. No. 2,321, as its seed parent, and "Uwe Seeler" as its pollen parent. The resulting seedling was asexually reproduced by budding. It holds its distinguishing characteristics through succeeding propagations by budding.

The new rose plant cv. Shreveport is particularly characterized by the following combination of characteristics: profusion of brightly-colored, well-formed flowers as described and illustrated herein; its abundance of leathery foliage and with foliage covering even the lowest branches thereby lending an overall attractiveness to the bush; its above average disease resistance in the Ontario, Calif. locale and its vigor providing an easy-care, easy-to-grow plant; and its upright habit and highly branched bush lend to its usefulness in the landscape.

This new cultivar may be distinguished from its seed parent, Zorina, by the following combination of characteristics:

Shreveport is classified as a hybrid Grandiflora, whereas seed parent (Zorina) is classed as a hybrid Floribunda.

Shreveport will only be utilized for garden decoration, whereas Zorina is used strictly as a variety for greenhouse cut rose production.

The seed parent, Zorina, bears flowers that are just under 3 inches in diameter whereas the flowers of the new cultivar (Shreveport) are significantly larger, of 3½ to 4½ inches in diameter.

The new rose Shreveport bears flowers of 44 to 51 petals, whereas Zorina bears flowers of significantly lower petalage (near 25).

The new cultivar rose (Shreveport) may be distinguished from its pollen parent (Uwe Seeler) by the following combination of characteristics:

Uwe Seeler bears flowers with 25 to 35 petals, whereas Shreveport bears flowers of significantly higher petalage (44 to 51) essentially as described and illustrated herein.

Whereas the new rose is classified as a hybrid Grandiflora, Uwe Seeler is classified as a hybrid Floribunda.

2

Whereas Uwe Seeler bears flowers of moderate fragrance, the new rose Shreveport bears flowers with only a slight tea fragrance.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the R.H.S. Colour Chart of The Royal Horticultural Society in London, England.

FLOWER

The new variety usually bears its flowers singly, sometimes three or more flowers per stem and in regular, flat clusters on strong, medium-length stems. Outdoors, the plant blooms almost continuously and gives abundant quantities during the growing season. It has a slight tea fragrance.

BUD

The peduncle is of short to average length, and average caliper, erect and stiff. It is moderately smooth with some stipitate glands; and it is between Yellow-Green 147A and Green 137A in color.

Before the calyx breaks, the bud is medium in size, and is of medium length, ovoid to globular in form, with foliaceous appendages and some stipitate glands on the surface of the bud. There are usually slender foliaceous parts extending beyond the tip of the bud equal to one-half or more of its length.

As the calyx breaks, the color is near Orange-Red, 32C.

The inner surfaces of the sepals have a fine, wooly tomentum; margins are lined with stipitate glands.

As the first petal opens, the bud is average in size and of medium length, ovoid to globular in form. The color on the outside of the basal attachment zone is near Yellow, 12B and suffuses to between Orange-Red, 32C and 32D. The inside surface shows a defined basal attachment zone of near Yellow, 12B that changes abruptly to between Orange-Red, 32C and 32D. The bud opens up well and is not retarded or prevented from opening by hot, wet or dry weather.

BLOOM

The size of the bloom when fully open is average in size, ranging from $3\frac{1}{2}$ to $4\frac{1}{2}$ inches. The petalage is very double, with from 44 to 51 petals and from 2 to 7 petaloids, arranged regularly. The bloom is very globular at first, becoming cupped. At first the petals remain tightly cupped, with tips reflexed slightly outward, becoming later at maturity loosely cupped with tips reflexed outward.

The petals are thick and with the inside slightly satiny and the outside slightly shiny. The outside petals are round to broadly obovate with a flat apex. The intermediate petals are broadly obovate and with a rounded to flat apex. The inside petals narrowly obovate with the apex having one or two notches. The colors may be modified by being bordered or margined or blotched, shaded and/or washed or tinted with other colors.

The paragraphs immediately following describe the color values observed in a flower newly opened in the month of August. The plant had been grown outdoors in Ontario, Calif.

The outside surface of the basal attachment zone is near Yellow, 12B and suffuses to between Orange-Red, 32D and Yellow-Orange 23C. The inner surface shows a defined basal attachment zone of near Yellow, 12A and changes abruptly to between Orange-Red 32C and 31C with edges exposed to sunlight occasionally blushing to deepening Orange-Red, 34C and 34A.

The outer surface and inner surfaces of the intermediate petals were the same as the outer and inner surfaces described above but with less of the intensified shadings at the petal edges. The outer and inner surfaces of the inner petals were as described above but without the deeper shading at the petal edges.

The paragraph immediately following describes color values observed in a bloom which had been open for three days, outdoors, in the month of August. The plant had been grown outdoors in Ontario, Calif.

The outer surface outside petal shows a basal attachment zone of near Yellow-Orange, 14C and suffuses to between Orange, 29B and 25B. The inner surface of the outside petal shows a basal attachment zone of near Yellow, 12B that abruptly changes to between Orange, 28C and Orange-Red 32D; occasionally areas near the edges exposed to sunlight blush to between Red, 41C and Orange-Red, 35B. The outer and inner surfaces of the inside petals are as described above for the outer and inner surfaces respectively of the outside petals.

The general color effect of the newly opened flower is between Orange-Red, 32C and 31C. The bloom after being three days open gives a general color effect which is near Orange-Red, 32D with occasional darker shadings near Red, 41C. The petals drop off cleanly and are not particularly affected by cold, hot, wet or dry weather.

In August, roses grown in the garden last on the bush from 4 to 5 days. Cut roses grown outdoors and kept at living-room temperatures will last from 3 to 5 days in the month of August.

REPRODUCTIVE ORGANS

An average number of stamens are arranged irregularly about the pistils and a few are mixed with petaloids.

The filaments are of medium length and most are with anthers.

The anthers are of small to medium size, all opening approximately at once; when moist, their color is near Yellow-Orange, 17B and when dry, their color is near Greyed-Orange, 163A.

Pollen is somewhat sparse in quantity and near Yellow-Orange, 17B in color.

There are an average to many number of pistils (approximately 75 in number).

The styles are moderately uneven, average in length and caliper and loosely bunched.

The stigma is near Yellow, 5B in color.

Most of the ovaries are in the calyx.

The hips are short, ovoid, have an inconspicuous neck and smooth, fleshy walls. Their color is near Yellow-Green, 146D.

The sepals fall soon and are of medium length, spear-shaped and recurved. The color on the inside is near Greyed-Green, 146D and on the outside is near Yellow-Green, 146D.

Seeds are few to average in number (from 8 to 15) and of medium size.

FOLIAGE

The compound leaves are borne very abundantly and usually comprise from three to five leaflets. The leaves are medium to large in size, heavy to somewhat leathery, and semi-glossy. The leaflets are oval in shape and have an acute apex and a round base. The margin is doubly serrate.

The mature foliage displays upon its upper surface a color which is between Yellow-Green, 147A and Green, 139A. The under surface is near Yellow-Green, 148B.

The color of the young foliage on its upper surface is between Yellow-Green, 148A and Green, 139A suffused with near Greyed-Purple, 184A. On its under surface, it is between Greyed-Purple, 183A and 187A.

The rachis is of average size, grooved on its upper side, with some stipitate glands on the edges; the under side is prickly and with a few stipitate glands.

The stipules are of medium length, very narrow having medium length points that turn out at an angle of more than 45°.

The plant displays a more than average resistance to mildew and blackspot compared to other commercial varieties grown under comparable conditions in Ontario, Calif.

GROWTH

The plant is of bushy upright habit and much branched. It displays a very vigorous growth. The canes are of medium to heavy caliper.

The main stems are near Greyed-Brown, 200D in color. They bear several large prickles which are of medium to long length, almost straight but hooked downwardly and with a medium-length, narrow base. The color is near Greyed-Brown, 200D. There are a few small prickles (Greyed-Brown, 200D in color) and no hairs.

The branches are of a color between Yellow-Green, 144A and Green, 137A. They bear several large prickles (near Yellow-Green, 146C in color) which are of medium to long length that are almost straight but hooked downwardly and with a medium-length, moderately narrow base. There are several small prickles of the same coloration and no hairs.

New shoots are near Yellow-Green, 144A suffused with near Greyed-Purple, 183A in color. They bear several large prickles, which are medium to long in length, almost straight but hooked downwardly, and having a medium-length, moderately narrow base and their color is near Greyed-Purple, 183A. There are several small prickles (of the same coloration) and a few Greyed-Purple, 183A hairs.

I claim:

1. A new and distinct variety of rose plant of the hybrid Grandiflora class, substantially as herein shown and described being particularly characterized in its profusion of brightly colored, leathery foliage covering even the lowest branches; its upright habit and highly branched bush; its above average resistance to disease and its vigor.

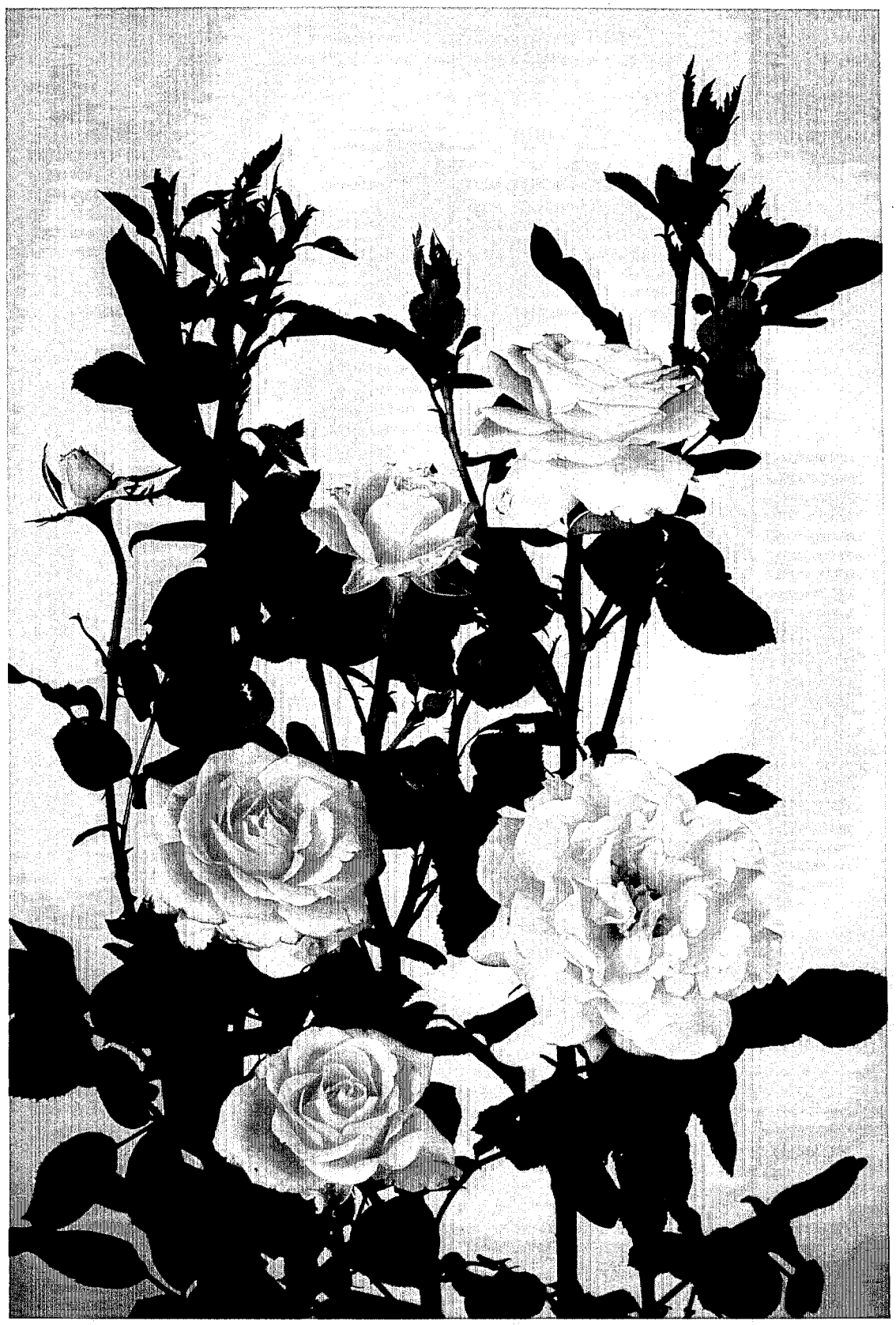

* * * * *